United States Patent [19]

Lustig et al.

[11] 4,185,384

[45] Jan. 29, 1980

[54] DENTAL ADJUSTMENT DEVICES

[75] Inventors: Leopold P. Lustig, 304 Greenwood St., Newton Centre, Mass. 02159; Elizabeth A. Bishop, Boston, Mass.

[73] Assignee: Leopold P. Lustig, Newton Centre, Mass.

[21] Appl. No.: 832,531

[22] Filed: Sep. 12, 1977

[51] Int. Cl.$^2$ .............................................. A61C 9/00
[52] U.S. Cl. ...................................................... 433/70
[58] Field of Search .......................... 32/17, 18, 19, 20

[56] References Cited

U.S. PATENT DOCUMENTS

| | | | |
|---|---|---|---|
| 1,910,740 | 5/1933 | Barsha | 32/19 |
| 3,046,658 | 7/1962 | Joffe | 32/19 |
| 3,126,631 | 3/1964 | McCarthy | 32/19 |
| 3,349,489 | 10/1967 | Shackelford | 32/19 |
| 3,421,223 | 1/1969 | Stark | 32/19 |
| 3,604,116 | 9/1971 | Shpuntoff | 32/19 |

FOREIGN PATENT DOCUMENTS 92350 10/1896 Fed. Rep. of Germany .............. 32/19

*Primary Examiner*—Russell R. Kinsey
*Assistant Examiner*—Michael J. Foycik
*Attorney, Agent, or Firm*—Alfred H. Rosen

[57] ABSTRACT

A thin articulating film which is susceptible of folding, wrinkling, crimping and the like is held taut in a generally U-shaped frame to which the film is permanently affixed at a part of its periphery. The edge of the film spanning the ends of the arms of the frame is unframed. The frame can be integral with the film. Devices for full-arch, anterior-arch and quadrant occlusal adjustment, and for contact adjustment between two adjacent teeth in one arch or another where one tooth or both may be a restoration, are described.

11 Claims, 11 Drawing Figures

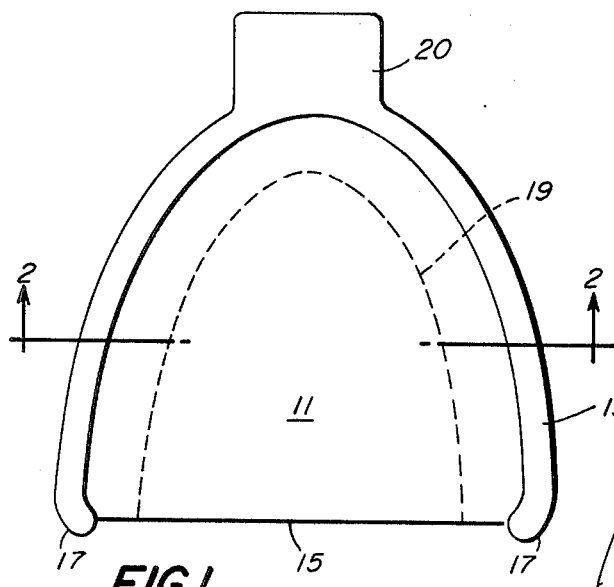
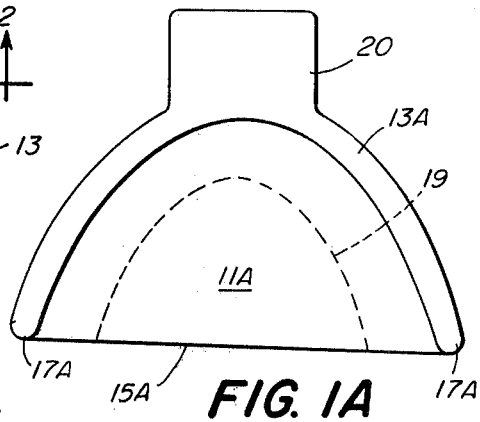
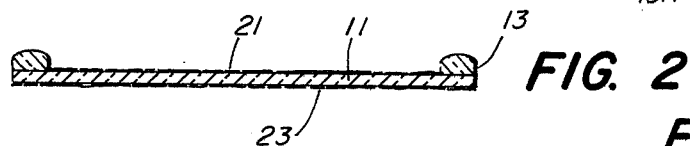
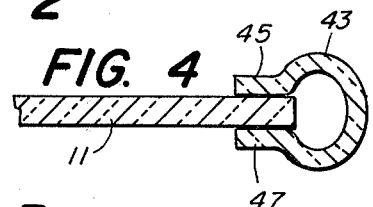
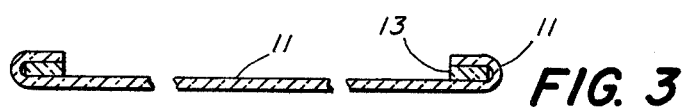
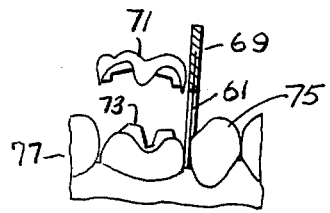
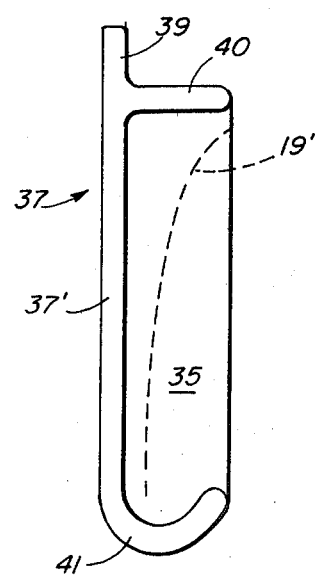
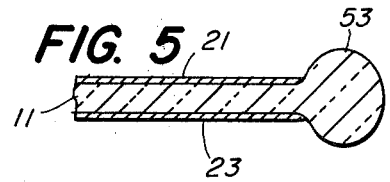
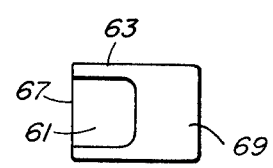
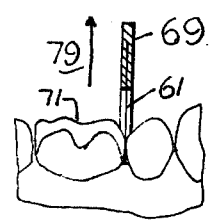
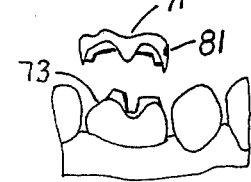

DENTAL ADJUSTMENT DEVICES

BACKGROUND OF THE INVENTION

Occlusal adjustment in reconstructive dentistry is aided with the use of articulating papers to establish occlusal contact points in test bites, and to expose interfering high spots in bite equilibration. Articulating papers are available in film-form having marking materials on one or both surfaces; where two marking materials are used, they can be of different colors; e.g.: one side red, the other side blue. Some articulating papers are available in films that are as thin as 15 microns thick, to aid in making fine adjustments by marking contact points with precision not available using thicker films. Some articulating papers are available for detecting bite intensity, for example, as shown in U.S. Pat. No. 3,959,881.

Very thin articulating papers must be used with care, to avoid damaging them, to prevent curling, crimping and folding the papers, and to avoid marking teeth erroneously. This problem is recognized in U.S. Pat. No. 2,633,637 (see column 1, at lines 25-31). In an attempt to overcome these problems, holders which resemble bite registration trays as used in taking impressions have been provided. Such holders are bulky, and especially where fine adjustments are to be made, they can interfere with the proper use of the articulating papers. A somewhat similar attempt to solve these problems is represented in U.S. Pat. No. 3,118,230, wherein is shown a three-dimensional device having a flat wall to engage between occlusal surfaces and side flanges forming a channel-like member.

GENERAL NATURE OF THE INVENTION

Our invention provides an occlusal adjustment device which comprises a flexible articulating film (or "paper") which is susceptible of folding, crimping and wrinkling, and which has marking means on one or both surfaces, as desired, and a substantially U-shaped or bow-shaped supporting frame permanently affixed to a portion of the periphery of the film, the film being held taut by the frame. The frame is stiffer than the film, but still flexible so that it can hold the film in a desired position in a mouth without folding, crimping or wrinkling the film, but is not so rigid as to give discomfort or prevent the film from conforming to the occlusal or contact surfaces of teeth being marked. The supporting frame can be attached to or integral with the film. The supporting frame can be fitted with a handle, as by a tab, so that it can be located by hand, and held in a desired location by hand, during the closure of the opposing arches in all functional movements. In the case of adjustment of contact areas between (e.g.) a completed restoration to be inserted and an existing tooth or another restoration this frame will expedite the adjustment by keeping the film taut thereby avoiding crimping, folding, or otherwise distorting the film. The framed articulating paper of this invention can be provided in sizes appropriate for use to mark occlusal contacts of full opposing dental arches, or opposing quadrants, or contact areas of two adjacent teeth. A tooth marking device of laminar construction with outer layers comprising woven fabric material is described in U.S. Pat. No. 3,421,223, wherein FIG. 6 shows a horseshoe-shaped pad of such laminar construction mounted in a wishbone-shaped holder. Unlike the present invention, that pad is not a flexible film that is susceptible of crimping or folding, and it is not held taut by the holder.

BRIEF DESCRIPTION OF THE DRAWINGS

FIG. 1 is a plan view of a full-mouth sized framed articulating film intended for occlusal adjustment;

FIG. 1A is a smaller embodiment comprised of the anterior portion of FIG. 1 intended for occlusal adjustment of the anterior arches only;

FIG. 2 is a section on line 2—2 of FIG. 1;

FIG. 3 is a section like FIG. 2 showing an alternative construction;

FIG. 4 is a partial section enlarged showing another construction;

FIG. 5 is a partial section enlarged showing still another construction;

FIG. 6 is a plan view of a quadrant-sized framed articulating paper;

FIG. 7 is a framed articulating paper sized for adjusting of contact areas between two adjacent teeth, such as adjustment of the proximal contact between a restoration to be inserted and an existing tooth and/or restoration; and FIG. 8A, 8B, and 8C illustrates steps in the use of the article of FIG. 7.

DETAILED DESCRIPTION OF THE DRAWINGS

In FIGS. 1 and 2 a sheet 11 of any available articulating paper or film is supported at a part but not all of its periphery by a frame 13, which may be made of any suitable material, including the same material as the film 11 but thicker to provide relatively more stiffness than the film. The frame 13 is U-shaped, or bow-shaped, and the film 11 fills the area within the frame and has an unframed edge 15 spanning the open ends 17, 17 of the arms of the frame. The ends 17 are rounded to prevent injury to the patient and to aid in displacing soft tissue when the device is placed in the mouth; thus to assure accurate placement of the film 11 between the occlusal surfaces without interference from or injury to surrounding soft tissue during placement of the device. The dashed line 19 represents the locus of a full arch in the mouth of a patient. The frame articulating film 11 can be placed while taut between the maxillary and mandibular arches and no part of the frame 13 will be located between the occlusal surfaces. The film 11 can be furnished on one or both of its surfaces with a pressure sensitive marking material 21, 23, of which many are known. One of the marking materials can be a powder-releasing material; that is, one of the surfaces of the film 11 can be coated with an adhesive, such as starch, and dusted just prior to use with a powder, such as talcum powder.

FIG. 1A shows a modification employing a part of the device of FIG. 1 for anterior-arch adjustment. The forward portions of film 11A and frame 13A terminating at rounded ends 17A, 17A, with film edge 15A free of the frame, provide the anterior-arch adjustment device. In each case, FIG. 1 or FIG. 1A, a handle 20 is fitted to the frame 13, 13A, at the bight portion of the frame arch, to aid in manual placement of the device between occlusal surfaces.

FIG. 3 illustrates an alternative construction in which the film 11 envelopes the frame 13. As is seen in FIG. 2, it is preferable to round off edges of the frame 13, to avoid injuring soft tissue in the patient's mouth. In FIG. 3 the film 11 covers the exposed edges of the frame.

In FIG. 4 the frame 43 is a generally U-shaped channel the arms 45, 47 of which form clamps to hold the film 11 between them.

In FIG. 5 the film 11 and frame 53 are made of the same material, the frame being thicker in cross-section to provide the desired support to the film. In this figure the marking materials 21, 23 are shown in place on the film.

In FIG. 6, the frame 37 is substantially U-shaped with its bight portion 37' longer than its inner and outer arms 40, 41, respectively, and has an outer portion of its longer bight extended beyond the film 35 to form a handle 39. The inner arm 41 of this frame can be located behind the last molar in the quadrant to be marked, and is curved to aid in placement of the device so as to assure that the film 35 will cover the last molars of the maxillary and mandibular quadrants. The locus of the quadrant is represented by the dashed line 19'.

FIG. 7 illustrates a framed articulating film 61 for adjustment of contact areas between an existing tooth and/or restoration, and a restoration to be inserted into or onto a prepared tooth or other preparation. A U-shaped frame 63 holds the film 61 taut at its periphery on all but one edge 67. An extended tab on the frame forms a handle 69, to facilitate locating the articulating film 61 between the two elements to be marked. In this case the frame can be placed between two adjacent dental elements.

When a casting, such as a crown for a tooth, is made, it is usually made slightly larger than needed, to avoid the possible necessity of adding material to it, should it be too small. It is, after all, easier to trim away excess material; but trimming must be done gradually and then only in areas where the crown is over-contoured. FIG. 8A, 8B, and 8C illustrates steps in using the article of FIG. 7 for this purpose. A crown 71 is to be fitted to a prepared tooth 73, which is located between two other teeth 75, 77, respectively. With the crown removed (i.e.: not in place on its tooth 73) the articulating film 61 is put in place between the prepared tooth 73 and an adjacent tooth 75, the handle 69 being used for this purpose, as shown in FIG. 8A. The crown 71 is then put in place on the prepared tooth 73, and the lateral surface of the crown which comes into contact with the adjacent tooth 75 now compresses the articulating film between the two teeth (FIG. 8B). Using the handle 69, the dentist then removes the framed articulating device by pulling upward as represented by an arrow 79. Where the crown made contact with the adjacent tooth 75 a spot 81 is marked by the articulating paper; that spot will be visible when the crown is removed from the prepared tooth 73 (FIG. 8C). This enables gradual trimming of the crown until the fit is corrected.

In embodiments of the invention that are intended for laboratory use, i.e.: for occlusal adjustments during wax-up procedures in the laboratory, the marking materials can be chosen with reduced regard to toxicity insofar as oral ingestion by the patient is concerned.

We claim:

1. A tooth marking device comprising a thin articulating film as little as 15 microns thick which is susceptible of folding, crimping and wrinkling in the manner of paper and the like, and permanently affixed to a portion of the periphery of said film, frame means that is flexible and stiffer than said film, said frame means being generally U-shaped with a bight portion and first and second arm portions and said film substantially filling the area within said frame means, said film being free of said frame means only at its edge spanning the free ends of said arm portions, and being fastened continuously to said bight and arm portions at all other parts of its periphery, and said film being held taut against crimping, wrinkling and folding by said frame means said frame means being flexible so as to permit said film to conform with occlusal or contact surfaces of teeth being marked.

2. A device according to claim 1 wherein said frame means is integral with said film.

3. A device according to claim 1 wherein said area is substantially coextensive with the occlusal area between two opposing maxillary and mandibular arches.

4. A device according to claim 1 having a tab extending from said frame means in the region of said bight portion, for manually holding said device in position.

5. A device according to claim 3 wherein said area is substantially coextensive with only the anterior segments of the opposing arches.

6. A device according to claim 1 wherein said film is elongated and generally rectangular for mating with a occlusal surfaces of a quadrant including molars, said film being supported by said frame means on one long edge and two short edges.

7. A device according to claim 1 wherein said frame means is generally U-shaped with a bight portion longer than its arm portions, wherein the bight portion extends beyond said film at one of said arms to form a handle.

8. A device according to claim 7 wherein one of said arms is curved to aid in placing said film between the occlusal surfaces of the last molars of a quadrant to be adjusted.

9. A device according to claim 1 wherein said film has powder-releasing marking means on one of its surfaces.

10. A device according to claim 1 wherein said area is substantially similar to the area of possible contact between two adjacent teeth either or both of which can be a restoration.

11. A unitary article of manufacture comprising a tooth-marking dental articulating film as little as 15 microns thick with a frame continuously attached to only a major portion of its periphery, a minor portion of the periphery of said film being unframed, said frame being flexible and stiffer than the film for providing flexible peripheral support to the film and holding the film taut in the frame and at the unframed portion of said periphery, so as to permit said film to conform with occlusal or contact surfaces of teeth being marked.

* * * * *